(12) United States Patent
Watson et al.

(10) Patent No.: US 8,408,707 B1
(45) Date of Patent: Apr. 2, 2013

(54) PREDICTION OF VISUAL ACUITY FROM WAVEFRONT ABERRATIONS

(75) Inventors: Andrew B. Watson, Los Gatos, CA (US); Albert J. Ahumada, Mountain View, CA (US)

(73) Assignee: The United States of America as Represented by the Administrator of the National Aeronautics and Space Administration (NASA), Washington, DC (US)

( * ) Notice: Subject to any disclaimer, the term of this patent is extended or adjusted under 35 U.S.C. 154(b) by 37 days.

(21) Appl. No.: 12/428,441

(22) Filed: Apr. 22, 2009

(51) Int. Cl.
*A61B 3/00* (2006.01)
*A61B 3/02* (2006.01)

(52) U.S. Cl. .................. 351/246; 351/239; 351/241

(58) Field of Classification Search .............. 351/239, 351/241, 246
See application file for complete search history.

(56) References Cited

U.S. PATENT DOCUMENTS

| | | | |
|---|---|---|---|
| 3,905,688 | A | 9/1975 | Decker et al. |
| 4,239,351 | A | 12/1980 | Williams et al. |
| 5,121,981 | A | 6/1992 | Waltuck et al. |
| 5,309,185 | A | 5/1994 | Harper et al. |
| 6,142,631 | A | 11/2000 | Murdoch et al. |
| 7,470,026 | B2 * | 12/2008 | Kaido et al. ............ 351/223 |

OTHER PUBLICATIONS

Cheng, et al., Predicting subjective judgment of best focus with objective image quality metrics, Journal of Vision, Apr. 23, 2004, 310-321, 4, http://journalofvision.org/4/4/7/, 2004 ARVO.
Guirao, et al., A Method to Predict Refractive Errors from Wave Aberration Data, Optometry and Vision Science, Jan. 2003, 36-42, 80-1, 2003 American Academy of Optometry.
Marsack, et al., Metrics of optical quality derived from wave aberrations predict visual performance, Journal of Vision, Apr. 23, 2004, 322-328, 4, http://journalofvision.org/4/4/8/, ARVO 2004.
Thibos, et al., Accuracy and precision of objective refraction from wavefront abberations, Journal of Vision, Apr. 23, 2004, 329-351, 4, http://journalofvision.org/4/4/9/, 2004 ARVO.
Dalimier, et al., Use of a customized vision model to analyze the effects of higher-order ocular aberrations and neural filtering on contrast threshold performance, J. Opt. Soc. Am. A, Jul. 23, 2008, 2078-2086, 25-8.
Nestares, et al., Bayesian Model of Snellen Visual Acuity, J. Opt. Soc. Am. A, Jul. 2003, 1371-1381, 20-7, 2003 Optical Society of America.
Applegate, et al., Metrics of retinal image quality predict visual performance in eyes with 20/17 or better acuity, Optom. Vision Sci., Sep. 2006, 635-640, 83, 2006 American Academy of Optometry.

* cited by examiner

*Primary Examiner* — Jack Dinh
(74) *Attorney, Agent, or Firm* — John F. Schipper; Robert M. Padilla; Christopher J. Menke

(57) ABSTRACT

A method for generating a visual acuity metric, based on wavefront aberrations (WFAs), associated with a test subject and representing classes of imperfections, such as defocus, astigmatism, coma and spherical aberrations, of the subject's visual system. The metric allows choices of different image template, can predict acuity for different target probabilities, can incorporate different and possibly subject-specific neural transfer functions, can predict acuity for different subject templates, and incorporates a model of the optotype identification task.

6 Claims, 3 Drawing Sheets

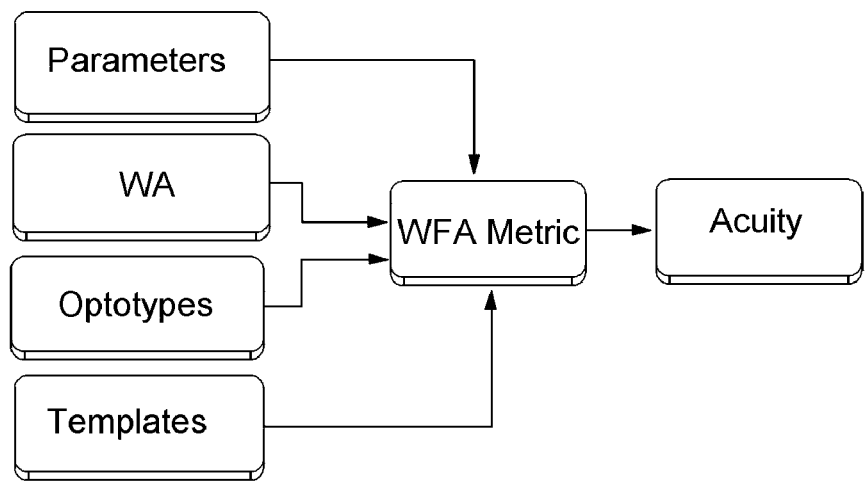
FIG. 1
CDHKNORSVZ
FIG. 2
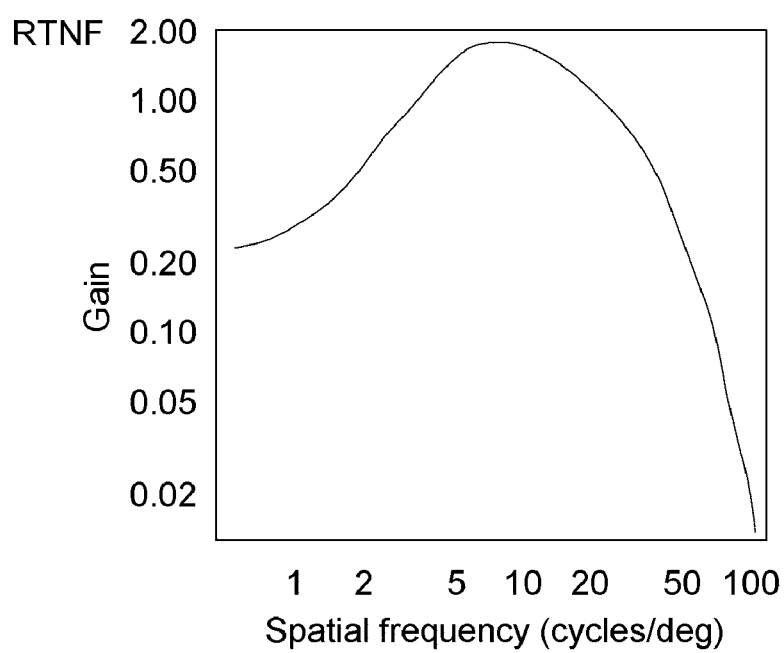
FIG. 4

PREDICTION OF VISUAL ACUITY FROM WAVEFRONT ABERRATIONS

ORIGIN OF THE INVENTION

This invention was made by one or more employees of the U.S. government. The U.S. government has the right to make, use and/or sell the invention described herein without payment of compensation, including but not limited to payment of royalties.

FIELD OF THE INVENTION

This invention relates to visual acuity of a human or other animal, based on wavefront aberrations associated with the animal's visual imaging system.

BACKGROUND OF THE INVENTION

It is now possible to routinely measure the monochromatic aberrations of the human eye. However, one cannot yet measure the visual acuity that will result from a given set of wavefront aberrations. One reason to seek a prediction of acuity from aberrations is the possibility of automated objective measurement of visual acuity, and of automated prescription of sphero-cylindrical corrections. However, it has been shown that correcting the spherical and cylindrical components of the aberrations (equivalent to minimizing the RMS error of the wavefront) does not provide best acuity. Thus these automated procedures must await a more sophisticated metric that can predict acuity from an arbitrary set of aberrations.

In the last decade there has been a revolution in measurement and treatment of visual optical defects. This revolution has included the development of aberrometers simple enough to be used in the clinic, refinement of methods of laser surgery for optical correction, and development of various optical implants, notably intra-ocular lenses (IOL). In all of these, measurement and interpretation of wavefront aberrations (WFAs) has played an important role. They are a simple and comprehensive way of describing the state of the optical system. In spite of this, there is at present no accepted, reliable way of converting WFAs to visual acuity, which is a standard measure of quality of vision. The WFA Metric allows calculation of visual acuity from wavefront aberrations.

What is needed is an approach, including one or more metrics, that allows a prediction of visual acuity, for a human or other animal, based on estimated wavefront aberrations (WFAs) measured or otherwise determined for the test subject. Preferably, the approach should allow acuity predictions for different optotypes, such as Sloan letters, Snellen e's, Landolt C's, Lea symbols, Chinese or Japanese characters and others. Preferably, the approach should permit incorporation of different, possibly subject-specific, neural transfer functions.

SUMMARY OF THE INVENTION

These needs are met by the invention, which develops and applies an optical-based and neural-based metric that allows prediction of visual acuity of the subject. For a given choice of an optotype set (e.g., Sloan letters), an optical transfer function $OTF(x,y)$ is generated, using Zernike polynomials and the associated Zernike coefficients and a specification of a pupil aperture image $PA(x,y)$ for two dimensional coordinates $(x,y)$ for the subject. A generalized pupil image and associated point spread function $PSF(x,y)$ is computed, from which an OTF is computed.

A neural transfer function $NTF(x,y)$ is specified, and a total transfer function $TTF(x,y)$ is computed as a product of the OTF and the NTF. A proportion correct function $P(k)$ is estimated from the neural images and a noise value, using one of three or more methods for such estimation. A probability criterion P(target) for measurement of visual acuity is specified, normally between 0.5 and 0.8. A numerical procedure returns a final index value j (final), which is converted to an estimate of acuity using a standard logMAR calculation. The output of the logMAR computation is a WFA metric that provides an estimate of visual acuity for the subject.

The metric(s) developed here is designed to predict symbol acuity from wavefront aberrations. One embodiment of the metric relies on Monte Carlo simulations of a decision process and relies on an ideal observer, limited by optics, neural filtering, and neural noise. A second metric is a deterministic calculation involving optics, symbols, and a hypothetical neural contrast sensitivity function CSF.

A WFA Metric is an algorithm for estimating the visual acuity of an individual with a particular set of visual wavefront aberrations (WFAs). The WFAs represent arbitrary imperfections in an optical system, and can include low order aberrations, such as defocus and astigmatism, as well as high order aberrations, such as coma and spherical aberration. WFAs can now be measured routinely with an instrument called an aberrometer. In modern practice, the WFAs are represented as a sum of Zernike polynomials $Z(x,y)$, each multiplied by a Zernike coefficient. A typical measurement on the eye of a subject will consist of a list of about 16 numbers, which are the coefficients of the polynomials. The WFA Metric converts the list of numbers into an estimate of the visual acuity of the subject. If changes are planned to the WFA of the subject (through surgery or optical aids) the predicted change in visual acuity can be calculated.

BRIEF DESCRIPTION OF THE DRAWINGS

FIG. 1 illustrates an embodiment of a structure for computation of a WFA metric according to the invention.

FIG. 2 illustrates the ten Sloan letters, expressed in a sans serif font, that provide one of the optotype sets that can be used with the invention.

FIG. 4 graphically illustrates a representative radial neural transfer function.

DESCRIPTION OF THE INVENTION

0. Notation and Terminology

Figure 3A:
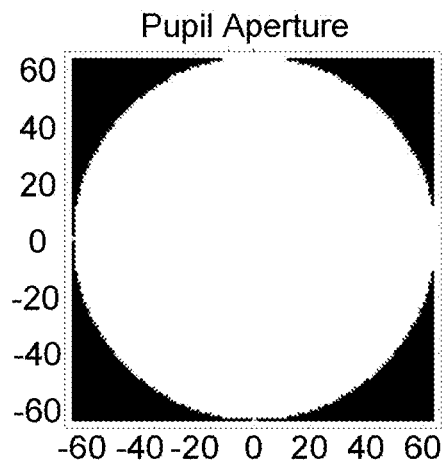
FIGS. 3A-3E illustrate steps in creation of the OTF.
Figure 3B:
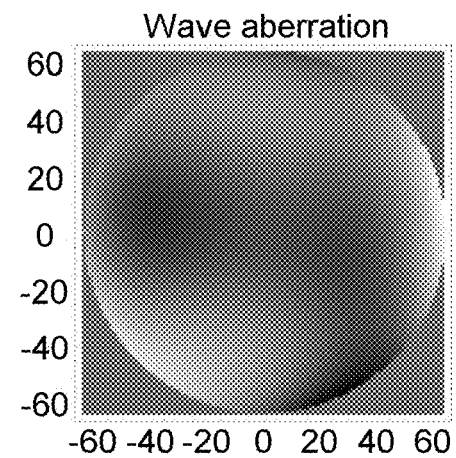
Figure 3C:
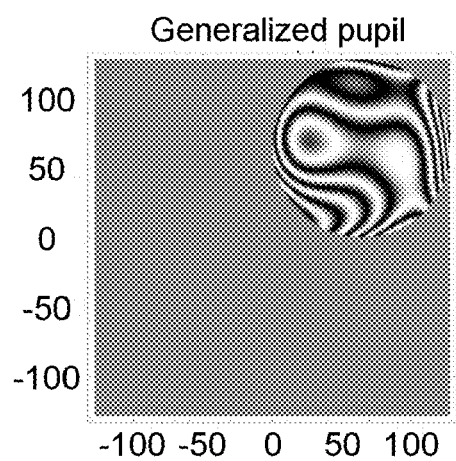
Figure 3D:
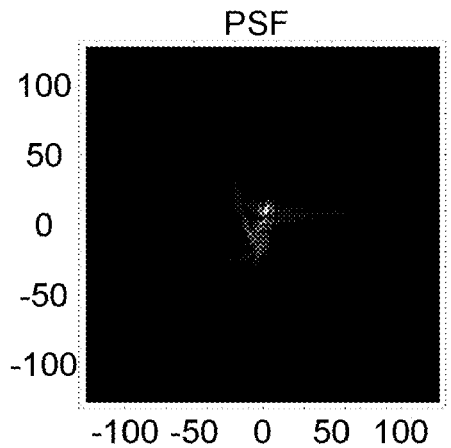
Figure 3E:
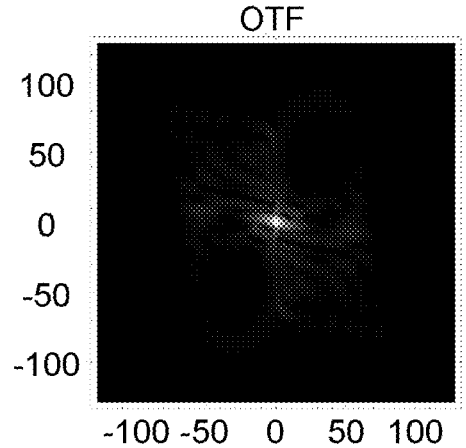

In this presentation, an "image" refers to a finite discrete digital image represented by a two-dimensional array of integers or real numbers. It has a width and height measured in pixels. Where the size is specified it will be given as a list {rows,columns}. The image has a resolution measured in pixels/degree. The pixel indices of the image are x (columns) and y (rows). Images will usually be an even number of pixels wide and tall. If the image size is {2h,2h}, then the indices x and y each follow the sequence $\{-h, \ldots, 0, \ldots, -h-1\}$. This places the origin of the image at the center. An image may be written with explicit row and column arguments $A(x,y)$, or without the coordinates as A.

In this presentation, a dft refers to a two-dimensional finite discrete digital array of complex numbers representing a Discrete Fourier Transform (DFT). It has a width and height measured in pixels. Where the size is specified it will be given as a list {rows,columns}. A dft has a resolution measured in pixels/cycle/degree. The pixel indices of the dft are a (columns) and v (rows). Dfts will usually be an even number of pixels wide and tall. If the dft size is {2h,2h}, then the indices u and v each follow the sequence {0, ..., h−1, −h ..., −−1}. This places the origin of the dft at the first pixel. This is the conventional ordering of indices in the output of the Fast Fourier Transform (FFT) operator. The FFT is a particular algorithm for implementation of the DFT. In the body of this document we refer to the DFT, but this will usually be implemented by the FFT.

In this presentation, vectors will be written with one subscript $A_k$, and matrices will be written with two subscripts $A_{j,k}$, where the first subscript indicates the matrix row. Frequently, we will deal with vectors or matrices whose elements are images, in which case the image coordinates x,y are omitted.

We make use of the notation A:B to indicate Frobenius inner product of two matrices $$A:B = \sum_y \sum_x A(x, y) B(x, y)$$

This is useful to describe a sum over pixels of the product of two images. The modulus or norm of an image is given by $$\|A\| = \sqrt{A:A}$$

1. Inputs and Output

The WFA metric has four inputs. A first input is a set of wavefront aberrations, represented as a weighted sum of Zernike coefficients $z_n(x,y)$. A second input is a set of optotypes, represented in a standard graphic format, such as a font description, a set of raster images, or graphic language descriptors. One example set of optotypes is the Sloan font for the letters {C, D, H, K, N, O, R, S, V, Z}, a set often used in the measurement of acuity). A third input is a set of templates, equal in number to the number of optotypes in the set. By default, the templates are derived from the optotype set and are not a distinct input. A fourth input is a set of parameters, some of which may have default values that are permanently stored within the program. Some parameters may be changed on every calculation of the metric, while others are unlikely to be changed often. The parameters are described throughout this description.

A single output, the visual acuity, is expressed as a decimal acuity or log of decimal acuity (logMAR). An overall system structure is shown in FIG. 1.

2. Overview of the Algorithm a. Generate the Optical Transfer Function (OTF)
b. Generate the Neural Transfer Function (NTF)
c. Generate the Total Transfer function (TTF)
d. Define the Proportion Correct function P(size)
e. Find the size for which P(size)≈$P_{target}$
Each of these steps is described in detail in the following.

3. Select a Set of Optotypes

The optotypes are a set of graphic symbols that the human observer is asked to identify in the course of an acuity test. Examples are Sloan letters, Snellen e's, Landolt Cs, Lea symbols, Chinese or Japanese characters, or other pictograms of various sorts. Each optotype set will have a fixed number K of elements, and a defined size specification.

By way of example, the optotype set used here is the Sloan letters {C, D, H, K, N, O, R, S, V, Z}, with K=10. These letters are shown in FIG. 2. Each Sloan letter has a stroke width MAR, expressed in minutes of arc of visual angle, and each letter is 5 MAR tall by 5 MAR wide. The size specification used here is $\log_{10}$ MAR, expressed as $$\log MAR(mar) = \log_{10}(mar)$$

4. Determine the Usable Range of Optotype Sizes

The usable range will be limited by the resolution and size of the PSF image. As discussed below, these are determined by the pupil size, the wavelength (λ), and the pupil magnification (m). If the PSF image has a width of r, expressed in pixels, and d in degrees, the smallest stroke-width possible is one pixel, or $$\log MAR_{min} = \log_{10}\left(\frac{60d}{r}\right)$$

The largest stroke-width will be one fifth width of the largest character, which will be one half the width of the PSF image; a margin is required to accommodate blur and to avoid wrap-around so that $$\log MAR_{max} = \log_{10}(6d)$$

It is sometimes convenient to adopt a positive integer index that corresponds to size. One example is computing logMAR in steps of 1/20. In that scheme, the minimum and maximum indices would be $$\text{index}_{min} = \text{Ceiling}(20 \log MAR_{min})$$

$$\text{index}_{max} = \text{Floor}(20 \log MAR_{max})$$

The index l then extends from 1 to $l_{max}$=$\text{index}_{max}$−$\text{index}_{min}$+1, and log MAR is given by $$\log MAR = \frac{l + \text{index}_{min} - 1}{20}, \quad \text{where } l = 1, \ldots, l_{max}$$

Using the default parameters, the PSF image will have a width of 256 pixels, and a width of 0.815525 deg. With these values $$\text{index}_{min} = -14$$

$$\text{index}_{max} = 13$$

The size index l will have values between 1 and $l_{max}$=28 for this example.

5. Generate the Optical Transfer Function (OTF)

The mathematical operations required to generate an optical transfer function (OTF) from a set of Zernike polynomials are well known. Graphs of the results at several stages are shown in FIGS. 3A-3E.

a. Create the Pupil Aperture Image PA(x,y). The image is of size {2h,2h}, where h is the half width of the pupil aperture image, expressed in pixels, $$PA(x, y) = 1 \text{ if } \sqrt{x^2+y^2}/h \le 1, \; x \text{ and } y \text{ integers } \in \{-h, \ldots 0, \ldots h-1\}$$
$$= 0 \text{ otherwise}$$

b. From the set of Zernike coefficients $C=\{c_0, c_1, c_2, \ldots, c_N\}$ (expressed in microns), create a discrete digital image of the Wavefront Aberration Image WA(x,y), with image size $\{2h, 2h\}$. If the Zernike polynomials $z_n(x,y)$ are identified by single index (the mode) n=0, ... N; and if the $c_k$ are the coefficients of the individual polynomials, then $$WA(x, y) = \sum_{n=1}^{N} c_n z_n(x, y)$$

We make use of the standard form of the Zernike polynomials as defined by Thibos, 2002, Jour. Of Optical Society of America.

c. Compute the Generalized pupil image GP(x,y)

$$GP(x, y) = PA(x, y) epx\left[\frac{i2\pi}{\lambda 10^{-3}} WA(xv,)\right]$$

where $\lambda$ is the wavelength of light in nm used to illuminate the optotype set.

d. Pad the image on the left and top with zeros to create an image of size $\{2hm, 2hm\}$. The parameter m is the pupil magnification.

e. Compute the Point Spread Function PSF(x,y)

$$PSF(x,y) = |DFT[GP(x,y)]|^2$$

where DFT is the Discrete Fourier Transform operator.

f. Normalize the PSF.

$$\overline{PSF}(x, y) = \frac{PSF(x, y)}{\|PSF(x, y)\|}$$

g. Compute the Optical Transfer Function OTF(u,v)

$$OTF(u,v) = 2hm DFT[\overline{PSF}(x,y)]$$

This result is a complex image of size $\{2hm, 2hm\}$.
The height and width of the PSF image in degrees of visual angle is given by $$d = \frac{h360\lambda 10^{-6}}{p\pi}$$

where p is the pupil diameter in mm. The height and width of the PSF image in pixels is given by $$r = 2hm$$

where h is a half-width. The resolution of the PSF image in pixels/degree is $$v = \frac{r}{d} = \frac{2\pi mp}{360\lambda 10^{-6}}$$

6. Generate the Neural Transfer Function (NTF)

a. The Radial Neural Transfer Function RNTF(u,v) is a two-dimensional real dft given by $$RNTF(u, v) = gain\left(\exp\left[-\left(\frac{f}{f_0}\right)^b\right] - loss \exp\left[-\left(\frac{f}{f_1}\right)^2\right]\right)$$

where gain, $f_0$, $f_1$, b, and loss are parameters. An example of this function is shown graphically in FIG. 4.

b. The Oblique Effect Filter OEF(u,v) is a two-dimensional real dft given by $$OEF(u, v) = OEF(f, \theta) = 1 - \left(1 - \exp\left(-\frac{f - \text{corner}}{\text{slope}}\right)\right)\sin(2\theta) \text{ if } f \ge \text{corner}$$
$$= 1 \text{ otherwise}$$

$$f = \sqrt{u^2 + v^2}$$

$$\theta = \arctan(u,v)$$

where corner and slope are parameters.

c. Compute the Neural Transfer Function NTF(u,v), a two-dimensional real dft given by $$NTF(u,v) = RNTF(u,v) OEF(u,v)$$

7. Generate the Total Transfer Function (TTF)

The Total Transfer Function is given by $$TTF(u,v) = OTF(u,v) NTF(u,v)$$

8. Define the Proportion Correct Function P(k)

The steps in evaluation of the P(k) function are as follows, and are diagrammed in FIG. 5.

a. Given a size index 1, create K optotype images $O_k(x,y)$. This may be done by rendering images from a graphic description, or the images may be pre-computed. Each image is of size $\{r,r\}$. See above for a definition of the optotype size index 1.

b. Create the K Neural Images $S_k(x,y)$ by computing the DFT of the each optotype image $O_k$, multiplying by the TTF, and taking the inverse DFT, $$S_k = IDFT[DFT[O_k]TTF]$$

where DFT is the DFT operation and IDFT is the Inverse DFT operation.

c. Create the K template images $T_k$. By default, these are identical to the Neural Images $S_k$.

d. Compute the normalized templates. Each template is divided by its norm, equal to the square root of the sum of the squares of all its pixels.

$$\overline{T}_k = \frac{T_k}{\|T_k\|}$$

e. Compute the matrix of normalized template cross-correlations $W_{j,k}$ $$W_{j,k} = \overline{T}_j \cdot \overline{T}_k$$

f. Create an array of cross-correlations between each neural images and each template. Note that the row indexes the neural image and the column, the template.

$$R_{j,k} = S_j \cdot T_k$$

g. At this point two or more methods are available, which we identify as methods 1 and 2.

Method 1.

i. Subtract each value from the main diagonal entry in the same row, and divide by a factor that includes the parameter σ (default value≈1). There are two possible versions of a matrix D, identified by subscripts 1 and 2.

$$D_{1,j,k} = \frac{R_{j,j} - R_{j,k}}{\sigma \sqrt{1 - W_{j,k}^2}}$$

ii. The probability correct for optotype j is given by $$P_{1,j} = \int_{-\infty}^{\infty} f(t) \prod_{k \neq j} F(t - D_{1,j,k}) dt$$

where f(t) and F(t) are probability density function and cumulative probability

Method 2

$$D_{2,j,k} = \frac{R_{j,j} - R_{j,k}}{\sigma \sqrt{2} \sqrt{1 - W_{j,k}}}$$

$$P_{2,j} = \prod_{k \neq j} F(D_{2,j,k})$$

The final value of P is given by $$P = \frac{1}{K} \sum_{k=1}^{K} P_k$$

9. Find the Size for which P≈P_target

The parameter $P_{target}$ is the criterion probability for measurement of visual acuity. It is usually set to a value between 0.5 and 0.8. This value will depend upon the number K of optotypes and must be greater than 1/K (the probability of getting the right answer by guessing). For the Sloan letters, a default value $P_{target}$=0.55 is used. Various efficient iterative procedures may be used to locate the value of size for which P≈P_{target}. Here we describe the method of bisection, though other methods may be used.

$l_{low} = 1$ $l_{high} = l_{max}$ $P_{low} = P(l_{low})$ $P_{high} = P(l_{high})$ begin loop If $l_{high} - l_{low} = 1$, exit and return $l_{final} = l_{low} + \frac{l_{high} - l_{low}}{P_{high} - P_{low}}(p_t - p_{low})$ $$l_{mid} = \text{Round}\left[\frac{l_{high} + l_{low}}{2}\right]$$

$P_{mid} = P(l_{mid})$

If $P_{mid} < P_{target}$, $l_{low} = l_{mid}$ $P_{low} = (l_{low})$ otherwise $l_{high} = l_{mid}$ $P_{high} = P(l_{high})$ Go to begin loop The returned value of $l_{final}$ can then be converted to an acuity in logMAR using the Equation above. This is the output of the WFA Metric.

Figure 5:
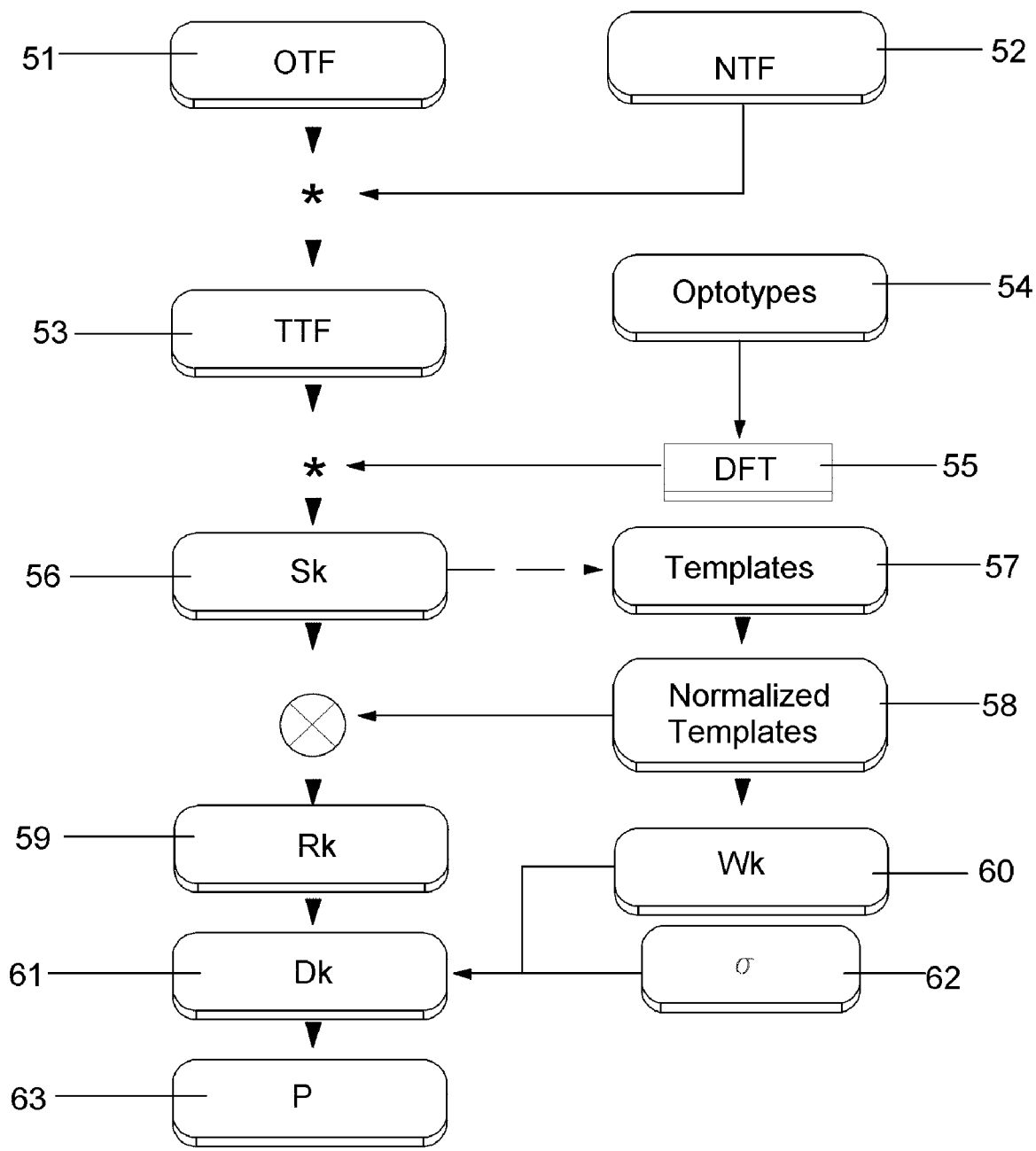
FIG. 5 is an embodiment of a procedure for evaluation of a probability correct index for one size optotype.

FIG. 5 illustrates a sequence of steps of a procedure for practicing the invention. In step 51, an OTF is generated. In step 52, an NTF is generated and is multiplied by the OTF, to form a TTF (step 53). In step 54, a set of optotypes is and is subjected to a DFT process, in step 55. In step 56, the processed optotypes are used to form images $S_j$ of the optotypes. In step 57, the images $S_j$ are used to create a set of templates $T_k$, and normalized templates $T_k^*$ are created in step 58. Cross-correlations $R_{j,k}$ of the images $S_j$ and the normalized templates $T_k^*$ are formed, in step 59. In step 60, cross-correlations $W_k$ of the normalized templates $T_k^*$. Normalized difference matrices $D_{j,k}$ are formed from the cross-correlation matrix $R_{j,k}$ are formed in step 61, using information from the cross-correlations $W_k$. and a statistical parameter σ, in step 62. In step 63, a probability P associated with measurement of visual acuity is computed.

10. Unique Features of the WFA Metric

The WFA metric is the only known metric to compute acuity from wavefronts that:
(i) incorporates a model of the optotype identification task
(ii) can predict acuity for different target probabilities
(iii) can predict acuity for different optotypes
(iv) allows user specification of optotypes
(v) can incorporate different and possibly subject-specific neural transfer functions
(vi) can predict acuity for different subject templates The template matching algorithm that is fundamental to this metric may have other uses in predicting performance in identification tasks.

| Parameter | Default value | Unit | Definition |
|---|---|---|---|
| K | | | number of optotypes |
| k | | | index of optotpye, 1, . . . , K |
| l | 556 | nm | wavelength |
| p | 5 | mm | diameter of pupil |
| h | 64 | pixels | half width of pupil image |
| m | 2 | | magnification |
| d | derived | degrees | size of the PSF image |

-continued

| Parameter | Default value | Unit | Definition |
|---|---|---|---|
| r | 2 m h | pixels | size of the PSF image |
| v | r/d | pixels/deg | resolution of PSF image |
| corner | 13.5715 | cycles/deg | oblique effect parameter |
| slope | 3.481 | | oblique effect parameter |
| gain | 3.149614 | | NTF parameter |
| loss | 0.9260249 | | NTF parameter |
| $f_0$ | 35.869213 | | NTF parameter |
| $f_1$ | 5.412887 | | NTF parameter |
| b | 1.064181 | | NTF parameter |
| l | | | optotype size index |
| WA | | image | wavefront aberration |
| PSF | | image | point spread function |
| PA | | image | pupil aperture |
| GP | | complex image | generalized pupil |
| TTF | | dft | total transfer function |
| NTF | | dft | neural transfer function |
| OTF | | dft | optical transfer function |
| OEF | | dft | oblique effect transfer function |
| $O_k$ | | | optotype with index k |
| $S_k$ | | | neural image of optotype |
| $T_k$ | | | template with index k |
| $\bar{T}_k$ | | | normalized template with index k |
| $W_{j,k}$ | | | cross-correlation between normalized templates |
| $R_{j,k}$ | | | cross-correlation between normalized templates and neural images |
| $D_{j,k}$ | | | template response distribution means |
| $P_j$ | | probability | probability correct for optotype with index k |
| P | | probability | probability correct for optotypes of one size |
| σ | | | noise standard deviation |
| $P_{target}$ | 0.55 | | criterion proportion correct |
| mar | | minutes | optotype stroke size |
| x,y | | | image pixel coordinates |
| u,v | | | dft pixel coordinates |
| j,k | | | row, column indices of matrices |
| $C_n$ | | | coefficient of Zernike polynomial n |
| $Z_n$ | | | Zernike polynomial n |

What is claimed is:

1. A method of predicting visual acuity of an imaging system, the method comprising:

providing a set of K optotypes, numbered k=1,..., K (K≧2) of a specified size, to be used to establish a reference set of symbols to estimate visual acuity, and providing a description or image $T_k(x,y)$ of each optotype, dependent upon location coordinates (x,y) associated with the optptype image produced by the imaging system;

constructing a Wavefront Aberration Image WAI(x,y) that manifests selected image aberrations associated with the imaging system;

computing a generalized pupil image GPI(x,y), with non-zero values confined to within a pupil aperture associated with the imaging system, that manifests the selected image aberrations and that is dependent upon at least one wavelength λ of light with which the image is viewed;

computing a Point Spread Function PSF(x,y) that is an absolute value squared of a Discrete Fourier Transform (DFT) of the image GPI(x,y);

computing a Normalized Point Spread Function NPSF(x,y), proportional to the Point Spread Function PSF (x,y), whose norm is 1;

computing an Optical Transfer Function OTF(u,v), expressed as a function of spatial frequency indice (u,v) in a Fourier transform plane, that is a Discrete Fourier Transform of the Normalized Point Spread Function NPSF (x,y), multiplied by a value h of original image size and multiplied by an image magnification index m;

generating a Radial Neural Transfer Function RNTF(u,v), where RNTF(u,v) satisfies the following conditions: (i) RNTF(u,v) is a continuous, non-negative function of a spatial frequency variable $f=[u^2+v^2]^{1/2}$; (ii) RNTF(u,v) has at least one value, f=f(max), for which NRTF(u,v) is a maximum; (iii) for 0<f<f(max), RNTF(u,v) is monotonically increasing in f; (iv) for f>f(max), and RNTF (u,v) is monotonically decreasing toward 0;

computing a Neural Transfer Function NTF(u,v) as a product of the Radial Neural Transfer Function RNTF (u,v) and an Oblique Effect Filter function OER(u,v) that compensates for viewing angle of the-original optotype image;

generating a Total Transfer Function TTF(u,v), defined as a product of NTF(u,v) and the Optical Transfer Function OTF(u,v);

generating a Proportion Correct index PC(j), which presents a probability associated with a correct optotype that would be identififed by a subject having the Wavefront Aberration Image WAI(x,y) for at least one optotype(j).

2. The method of claim 1, wherein said step of constructing said Waveform Aberration Image WAI(x,y) comprises:

providing a Pupil Aperture Imaging characteristic function PA(x,y) that has a first value substantially equal to 1 within a pupil aperture of a test subject and has a second value substantially equal to 0 outside the pupil aperture of the test subject, where (x,y) are location coordinates;

providing a set of Zernike polynomials $Z_n(x,y)$ and associated coefficients $c_n$, and creating a discrete digital image a Wavefront Aberration Image WAI, defined as an error sum $$WAI(x,y) = \Sigma_n c_n Z_n(x,y);$$

where the coefficients $c_n$ are chosen to minimize a computed error between an image provided by said imaging system and the error sum;

computing a generalized pupil image GP, defined as $$GP(x,y) = PA(x,y) \exp\{2i WAI(x,y)/(\lambda/1000)\},$$

where λ refers to a wavelength used to illuminate the optotypes; and padding said image of each of said optotype on at least two adjacent edges of said image with zeroes to create an image of size $(\Delta x, \Delta y) = (mh, mh)$, where h represents an original image size, measured in a selected direction, and m is a multiplier index.

3. The method of claim 1, wherein said Oblique Effect Filter OEF(u,v) is determined by a procedure comprising forming $$OEF(u,v) = OEF1(f,\theta) = 1 - \{1 - \exp\{((\text{corner}) - f)/(\text{slope})\}\}\sin 2\theta$$

$$\text{if } f \geq (\text{corner})$$

$$= 1 \text{ otherwise}$$

$$f = (u^2+v^2)^{1/2}$$

$$\theta = \arctan(u,v),$$

where corner and slope are parameter.

4. The method of claim 1, wherein said process of generating said Proportion Correct index PC(j) comprises:

computing a neural image $S_j(x,y)$ $(j=1,\ldots,K)$ as an inverse DFT of a product of said Total Transfer Function TTF $(u,v)$ multiplied by a DFT of an optotype image $O_j(x,y)$;

computing a cross-correlation matrix between each of the neural images $S_j$ and each of said templates $T_k$, defined as $$R_{j,k}=S_j(x,y):T_k(x,y);$$

computing a cross-correlation matrix of each normalized template with each normalized template, $W_{j,k}=T_j:T_k$;

computing and normalizing a difference of matrix entries, $R_{j,j}-R_{j,k}$, between each diagonal entry $R_{j,j}$ and each entry $R_{j,k}$ in a corresponding row of the matrix $\{R_{j,k}\}$, to form a normalized difference matrix $D_{j,k}$;

$$D_{j,k}=\{R_{j,j}-R_{j,k}\}/\{\sigma\{1-W_{j,k}^2\}^{1/2}\},$$

where $\sigma$ is a statistical value that is provided or computed; and estimating a probability for estimation of a correct optotype by a subject by computing a probability value that is either (i) a product of functions of the matrices $D_{jk}$, or (ii) an integral, with an integrand equal to a normal statistical function, multiplied by the product of the functions of the matrices $D_{jk}$.

5. The method of claim 1, wherein said Radial Neural Transfer Function RNTF(u,v) is defined as $$RNTF(u,v)=(gain)\{\exp[-(f/f_0)^b-(loss)\exp[-(f/f_1)^2]\},$$

where $f=(u^2+v^2)^{1/2}$ is a spatial frequency and (gain), (loss), b, $f_0$ and $f_1$ are selected parameter values.

6. The method of claim 1, wherein said set of optotypes includes at least one of:

Sloan letters; Snellen E's; Landolt C's; and Lea symbols.

* * * * *